United States Patent
Goren et al.

(10) Patent No.: US 10,633,688 B2
(45) Date of Patent: Apr. 28, 2020

(54) SYSTEMS AND METHODS FOR PREDICTING RESPONSE TO MINOXIDIL FOR THE TREATMENT OF ANDROGENETIC ALOPECIA

(71) Applicant: Follea International, Irvine, CA (US)

(72) Inventors: Ofer A. Goren, Newport Beach, CA (US); John McCoy, Downey, CA (US); Philip Y. Tam, Rowland Heights, CA (US)

(73) Assignee: Follea International, Irvine, CA (US)

( * ) Notice: Subject to any disclaimer, the term of this patent is extended or adjusted under 35 U.S.C. 154(b) by 0 days.

(21) Appl. No.: 14/248,331

(22) Filed: Apr. 8, 2014

(65) Prior Publication Data

US 2014/0220609 A1    Aug. 7, 2014

Related U.S. Application Data

(63) Continuation-in-part of application No. 14/247,196, filed on Apr. 7, 2014, now Pat. No. 9,588,118, which is a continuation-in-part of application No. 13/245,783, filed on Sep. 26, 2011, now Pat. No. 8,691,518.

(60) Provisional application No. 61/386,451, filed on Sep. 24, 2010.

(51) Int. Cl.
    *C12Q 1/48*    (2006.01)
(52) U.S. Cl.
    CPC .................... *C12Q 1/48* (2013.01)
(58) Field of Classification Search
    CPC .................... C12Q 1/48; A61Q 7/00
    See application file for complete search history.

(56) References Cited

U.S. PATENT DOCUMENTS

| | | | |
|---|---|---|---|
| 4,849,347 A | 7/1989 | Familletti et al. | |
| 5,760,315 A | 6/1998 | Verheijden et al. | |
| 5,958,946 A | 9/1999 | Styczynski et al. | |
| 6,075,005 A * | 6/2000 | Lurie | 514/9.7 |
| 8,691,518 B2 | 4/2014 | Tam et al. | |
| 8,758,993 B2 | 10/2014 | Goren et al. | |
| 2011/0212167 A1 | 9/2011 | Ali et al. | |
| 2014/0023618 A1 | 1/2014 | Goren et al. | |
| 2014/0335537 A1 * | 11/2014 | Goren et al. | 435/7.4 |

FOREIGN PATENT DOCUMENTS

| | | |
|---|---|---|
| CA | 2233961 A1 | 4/1997 |
| SE | 1307181 B1 | 11/2005 |

OTHER PUBLICATIONS

Anderson et al., Sulfation of minoxidil by multiple human cytosolic sulfotransferases., Chem Biol Interact. (1998), vol. 109(1-3), pp. 53-67.

Frame et al., A simple Colorimetric Assay for Phenotyping the Major Human Thermostable Phenol Sulfotransferase (SULT1A1) Using Platelet Cytosols, Drug Metabolism and Disposition (2000), vol. 28, pp. 1063-1068.

Falany, C. N. et al., "Sulfation of Minoxidil by Human Liver Phenol Sulfotransferase," Biochemical Pharmacology, vol. 40, No. 5, 1990, pp. 1027-1032.

Johnson, G. A. et al., "Sulfation of Minoxidil Platelet Sulfotransferase," Clinica Chimica Acta, vol. 169, 1987, pp. 217-228.

Buhl et al. "Minoxidili Sulfate is the Active Metabolite that Stimulate Hair Follicles", Journal of Investigative Dermatology, 1009, vol. 95, pp. 553-557.

PCT International Search Report and Written Opinion in International Application No. PCT/US12/57399, dated Feb. 21, 2013.

PCT Invitation to Pay Additional Fees and, Where Applicable, Protest Fee, in International Application No. PCT/US12/57399, dated Nov. 29, 2012.

Office Action in U.S. Appl. No. 13/245,783, USPTO, Alexandria, VA, dated Aug. 8, 2013.

Randall et al. "Mechanism of Androgen Action in Cultured Dermal Papilla Cells Derived from Human Hair Follicles with Varying Responses to Androgens in Vivo", 1992. J. Invest Dermatol. 98:86S-91S.

Giulani et al. 2010. "Rutin efficacy in hair loss" J. Invest Dermatol. 130 Suppl 1, p. S102, #607.

Brozic et al. "Inhibitors of Aldo-Keto Reductases AKR1C1-AKR1C4", 2011. Current Med. chem 18:2554-2565.

Halim et al. "Imaging Induction of Cytoprotective Enzymes in Intact Human Cells: Coumberone, a Metabolic Reporter for Human AKR1C Enzymes Reveals Activation by Panaxytriol, an Active Component of Red Ginseng" 2008. JACS 130:14123-14128.

Eicheler et al. "5α-Reductase activity in the human hair follicle concentrates in the dermal papilla" 1998. Arch. Dermatol. Res. 290:126-132.

Rodriguez et al. "Expanding the use of fluorogenic enzyme reporter substrates to imaging metabolic flux changes: the activity measurement of 5α-steroid reductase in intact mammalian cells." 2010. ACS Chemical Biol. 5:1045-1052.

PCT International Search Report and Written Opinion in International Application No. PCT/US2012/060321, International Search Authority, Alexandria, VA, dated Mar. 29, 2013.

Office Action in U.S. Appl. No. 13/652,463, USPTO, Alexandria, VA, dated Jul. 25, 2013.

Baker, C.A., et al., "Minoxidil sulfation in the hair follicle," Skin Pharmacol 1994, 7, pp. 335-339.

Buhl, A.E., et al., "Minoxidil sulfotransferase activity influences the efficacy of Rogaine® topical solutions (TS)—enzyme studies using scalp and platelets," The Journal of Investigative Dermatology, 1994, 7, p. 534.

(Continued)

*Primary Examiner* — Ralph J Gitomer

(74) *Attorney, Agent, or Firm* — Buchanan Ingersoll & Rooney PC

(57) ABSTRACT

Methods, processes, systems, and apparatuses are disclosed for predicting minoxidil response in the treatment of androgenetic alopecia based on colorimetric assay for sulfotransferase activity. In particular, SULT1A1 activity may be used as an indicator of minoxidil response. A genetic test for alleles of the SULT1A1 gene may be performed to provide a more personalized therapy.

18 Claims, 3 Drawing Sheets

(56) References Cited

OTHER PUBLICATIONS

Dooley, T.P., et al., "Localization of minoxidil sulfotransferase in rat liver and the outer root sheath of anagen pelage and vibrissa follicles," The Society for Investigative Dermatology, Inc., 1991, 96, pp. 65-70.

Hebbring, S.J., et al., "Sulfotransferase gene copy number variation: pharmacogenetics and function," Cytogenet and Genome Research, 2008, 123, pp. 205-210.

Yu, X., et al., "Copy Number variation in sulfotransferase isoform IAI (SULTIAI) is significantly associated with enzymatic activity in Japanese subjects," Pharmacogenomics and Personalized Medicine, 2013, 6, pp. 9-24.

Goren, A., et al., "Novel enzymatic assay predicts minoxidil response in the treatment of androgenetic alopecia," Dermatologic Therapy, vol. ••, 2013, 4 pages.

Office Action (Restriction) in U.S. Appl. No. 13/843,908, dated Dec. 26, 2014.

\* cited by examiner

SYSTEMS AND METHODS FOR PREDICTING RESPONSE TO MINOXIDIL FOR THE TREATMENT OF ANDROGENETIC ALOPECIA

CROSS-REFERENCE TO RELATED APPLICATIONS

This application is a continuation-in-part of U.S. application Ser. No. 14/247,196, filed on Apr. 7, 2014, entitled "Devices for Performing Colorimetric Assay with Plucked Human Hair," which is incorporated herein by reference in its entirety, which is a continuation-in-part of U.S. patent application Ser. No. 13/245,783, filed on Sep. 26, 2011, entitled "Systems and Methods for Predicting Response to Minoxidil for the Treatment of Androgenetic Alopecia," which is incorporated herein by reference in its entirety, which claims priority to U.S. Provisional Application Ser. No. 61/386,451, filed on Sep. 24, 2010, titled "System and Method for Predicting Response to Minoxidil for the Treatment of Androgenetic Alopecia Based on a Rapid Colorimetric Assay."

TECHNICAL FIELD

The inventions described here relate to systems and methods for predicting minoxidil response in the treatment of androgenetic alopecia.

BACKGROUND

Androgenetic alopecia affects approximately 50% of the population by the age of 50. See Hoffmann R, Happle R., "Current understanding of androgenetic alopecia. Part II: clinical aspects and treatment," *Eur. J. Dermatol.* 2000: 10 (5): 410-417. Topical minoxidil is the most common drug used for the treatment of androgenic alopecia. Although topical minoxidil exhibits a good safety profile, the efficacy in the overall population remains relatively low at 30-40%. Clinical studies have shown that following 16 weeks of minoxidil (5%) mono-therapy approximately 38.6% of patients experience hair growth. See Olsen E A, Whiting D, Bergfeld W, et al., "A multicenter, randomized, placebo-controlled, double-blind clinical trial of a novel formulation of 5% minoxidil topical foam versus placebo in the treatment of androgenetic alopecia in men," *J. Am. Acad. Dermatol.* 2007: 57 (5): 767-774. To observe significant improvement in hair growth, minoxidil is typically used daily for a period of at least 3-4 months. Due to the significant time commitment and low response rate, a biomarker for predicting patient response prior to therapy would be advantageous.

The exact mechanism of action for minoxidil based treatment of androgenetic alopecia is not completely understood. However, in vitro studies have demonstrated that minoxidil sulfate is the active metabolite of minoxidil. See Buhl A E, Waldon D J, Baker C A, Johnson G A., "Minoxidil sulfate is the active metabolite that stimulates hair follicles, J. Invest. Dermatol. 1990: 95 (5): 553-577. The conversion of minoxidil to minoxidil sulfate is catalyzed by the enzyme minoxidil sulfotransferase (SULT1A1) in the hair follicle. See Baker C A, Uno H, Johnson G A., "Minoxidil sulfation in the hair follicle, Skin Pharmacol. 1994: 7(6): 335-339. Correlation between SULT1A1 expression in the scalp and minoxidil response has been reported. See Buhl A E, Baker C A, Dietz A J, Murray F T, Johnson G A, "Minoxidil sulfotransferase activity influences the efficiency of Rogaine® topical solutions (ts)—enzyme studies using scalp and platelets," J. Invest. Dermatol. 1994: 102: 534.

While minoxidil has also been approved by the FDA for treatment of female hair loss, for most women minoxidil is only marginally successful at retaining existing hair. Some men for whom minoxidil is less effective have been successfully treated with finasteride; however, the same cannot be said of females for whom minoxidil is ineffective. Studies have thus far failed to show the effectiveness of finasteride in the treatment of female androgenetic alopecia.

There are significant differences between male androgenetic alopecia and female androgenetic alopecia. Apart from the different baldness patterns, male and female alopecia follow a different mechanism. In men, alopecia is related to the normal high androgen levels in males, combined with an underlying sensitivity of the hair roots to androgens. Women, however, have roughly 10 times lower androgen levels than men, and the absolute amount of androgen is a less significant factor than the increased sensitivity of the hair roots to androgens.

Finasteride therapies that are successful at hair re-growth and maintenance in males have failed to show significant improvement in females. Further, for minoxidil therapy to be effective it often must be used for a prolonged period of time without knowing if it is effective.

Among various individuals, whether male or female, there is a broad variability in the response of different people to various hair loss treatments. This variability is presumed to be a result of genetic factors contributing to variable enzyme activity in the follicles, making a one-size-fits-all approach difficult to achieve. It would therefore be advantageous to be able to have an effective diagnostic and treatment method where patients could be selected and treated on the basis of criteria such as enzyme activity, which would identify some people as being likely to benefit from treatment by minoxidil and other drugs, while identifying other individuals in which treatment is not likely to be effective.

BRIEF SUMMARY

The inventions described here relate to systems and methods for predicting minoxidil response in the treatment of androgenetic alopecia, which in one embodiment may be based on a colorimetric assay. Various embodiments are possible, a number of which are exemplified here. In particular, variations in hair follicle sulfotransferase activity, and particularly SULT1A1 activity, may be used to predict the efficacy of minoxidil for the treatment of androgenetic alopecia.

In one embodiment, there is provided a method for selecting a treatment for a human subject suffering from androgenetic alopecia. This method may comprise obtaining a sample from the human subject, comprising one or more hairs that have been plucked from the human subject, said hairs comprising one or more hair follicles. A colorimetric assay may be performed to measure a sulfotransferase enzyme activity in the sample, thereby generating an activity value indicative of the sulfotransferase activity level in the sample, wherein the assay comprises the step of placing the sample in a reaction mixture comprising an indicator dye and minoxidil, and wherein during the assay, the indicator dye undergoes a color change that correlates with the amount of sulfotransferase activity level in the sample, and wherein the activity value correlates with said color change. The activity value may be compared to one or more standardized activity values, each standardized activity value representing either high or low expected minoxidil response for hair re-growth or retention for a class of human subjects including the human subject, thereby producing an indication of either high or low expected minoxidil response for hair re-growth or retention for the human subject at a particular dosage and form of minoxidil. The indication may be presented to the human subject.

In one particular embodiment, the sulfotransferase is SULT1A1. In a further embodiment, when the human subject exhibits low SULT1A1 activity, a test of a biological sample from the human subject may be performed, for the presence of a predetermined allele of the SULT1A1 gene. This allele may, in one particular example, be SULT1A1*2. In a further embodiment, if the human subject exhibits this allele, finasteride or some other non-minoxidil treatment may be prescribed. If the human subject does not exhibit this allele, another treatment may be prescribed that addresses environmental factors, such as the discontinuation of the use of salicylic acid.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted based on the text of the specification or the common knowledge within this field.

In the drawings, where like reference numerals refer to like reference in the specification.

DETAILED DESCRIPTION

Figure 1:
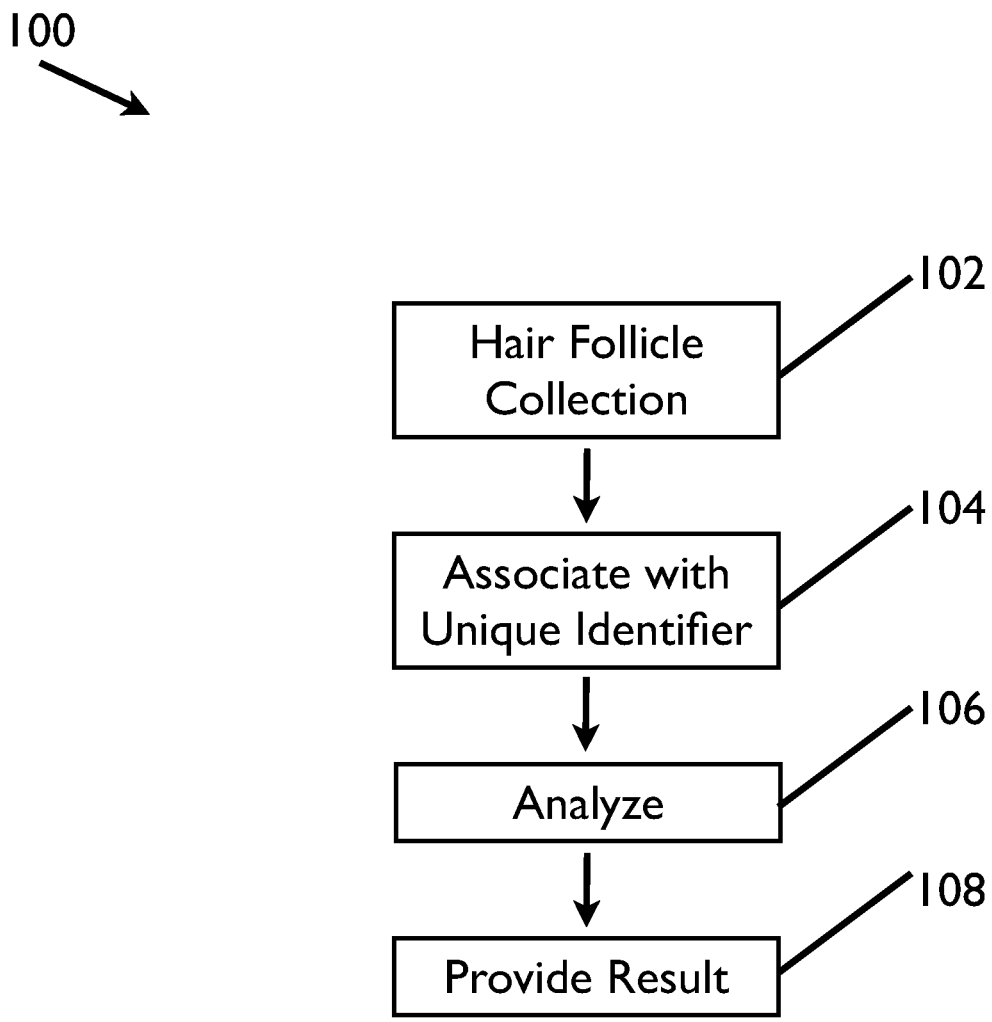
FIG. 1 is a flowchart showing a method of analyzing one or more hair follicles and providing a result.

Various example embodiments of the present inventions are described herein in the context of a therapy for androgenetic alopecia.

The description herein is provided in the context of a therapy for androgenetic alopecia. Those of ordinary skill in the art will realize that the following detailed description is illustrative only and is not intended to be in any way limiting. Other embodiments will readily suggest themselves to such skilled persons having the benefit of this disclosure. Reference will now be made in detail to implementations as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Such a development effort might be complex and time-consuming, but would nevertheless be a routine undertaking for those of ordinary skill in the art having the benefit of this disclosure.

Patients may be screened that will respond best to minoxidil therapy and thereby provide personalized effective therapy for hair loss. In one embodiment, a colorimetric assay of sulfotransferase activity, for example similar to that described in Frame L T, Ozawa S, Nowell S A, et al. "A simple colorimetric assay for phenotyping the major human thermostable phenol sulfotransferase (SULT1A1) using platelet cytosols, *Drug Metab. Dispos.* 2000: 28 (9): 1063-1068, may be used to measure the conversion of minoxidil in the hair root of a plucked human hair.

Expression of SULT1A1 has been localized to the outer root sheet. See Baker C A, Uno H, Johnson G A. Minoxidil sulfation in the hair follicle. Skin Pharmacol 1994: 7 (6): 335-339; Dooley T P, Walker C J, Hirshey S J, Falany C N, Diani A R, "Localization of minoxidil sulfotransferase in rat liver and the outer root sheath of anagen pelage and vibrissa follicles," J Invest. Dermatol. 1991: 96 (1): 65-70. Thus, minoxidil sulfate is expected to be abundant in plucked hair. In an assay, the conversion of minoxidil to minoxidil sulfate may be coupled to the conversion of p-nitrophenyl sulfate to p-nitrophenol, which can be quantified by optical absorbance at 405 nm. As such, sulfotransferase activity in the hair follicle would be a predictor of minoxidil response in AGA patients.

Response to minoxidil for the treatment of androgenetic alopecia has been associated with differences in scalp sulfotransferase activity. Therefore, a subject with a high level of minoxidil sulfotransferase activity will generate more minoxidil sulfate, and therefore will likely have a good response to minoxidil for the treatment of androgenetic alopecia. On the other hand, a subject with a low level of minoxidil sulfotransferase activity will not generate much minoxidil sulfate, and will likely have a poor response to minoxidil for the treatment of androgenetic alopecia.

Clinical trials with minoxidil for the treatment of androgenetic alopecia have shown statistically significant results for maintenance and growth of hair. Several studies have demonstrated the level of minoxidil sulfotransferase activity is significantly greater in patients responding to minoxidil for the treatment of androgenetic alopecia. As described herein, the assessment of hair re-growth is based on one or more of the following parameters: patient self assessment, physician assessment using a standardized scale, global photography assessment, hair diameter measurement, average hair length measurement, average hair diameter measurement, and hair weight measurements. The current inventions provide a method of using biochemical variations in minoxidil sulfotransferase activity as a drug response marker for minoxidil treatment of androgenetic alopecia. Based on the minoxidil sulfotransferase activity level, the method disclosed herein allows a physician or the patient to select the appropriate treatment and dosage thereof for the treatment of androgenetic alopecia.

In accordance with one approach described herein, a patient's hair follicle sample may be obtained. Preferably, at least two hair follicles may be obtained, so that if only one is analyzed, there will be at least one backup if needed.

The patient's hair follicle sample may be subjected to a colorimetric assay to determine the level of minoxidil sulfotransferase activity. A patient's hair follicle sample (from 1 to n hair follicles) may be placed in a reaction mixture containing about 50 mM potassium phosphate buffer (pH approximately 6.5), about 5 mM magnesium chloride, about 20 µM adenosine 3',5'-diphosphate (PAP) or adenosine 3'-phosphate, 5'-phosphosulfate (PAPS), about 5 mM p-nitrophenyl sulfate and about 0.1 mM minoxidil.

In one embodiment this reaction may take place in a transparent container with a lid or other opening in which the hair follicle samples may be inserted. In one non-limiting example, the total amount of liquid in the assay container may be about 0.2 ml.

As part of the above reaction, it is understood that in the presence of minoxidil sulfotransferase activity, p-nitrophenyl sulfate is converted to the colorimetric p-nitrophenol.

The reaction may be mixed and then incubated for approximately 4 to 16 hours at 37° C. depending on the number of hair follicles used in the assay. Mixing may be by any mixing means known in the art, including shaking the container. Where a shorter incubation time is required for a greater number of hair follicles. In one embodiment, an assay that uses one hair follicle may be incubated for approximately 16 hours. In another embodiment, an assay that uses two hair follicles may be incubated for approximately four hours.

After sample incubation, the reaction may be stopped by addition of about $\frac{1}{10}$th volume of approximately 0.25 M Tris-HCl buffer, pH 8.7, and mixed. The pH may vary, in one embodiment between 8.5 to 9.0. Especially if the assay is performed or sold as part of a kit, the basic buffer may be provided as a separate container for pouring into the assay reaction container. In another embodiment, the basic buffer may be provided in a pre-loaded syringe, to be injected into the main reaction container at the appropriate time, either by manually pushing a plunger, or by some automatic or computerized control.

The absorbance at about 405 nm may then be read with a spectrophotometer or compared to a reference color card with a range of intensities corresponding to minoxidil sulfotransferase activity. Patients with a relatively high level of sulfotransferase activity will have a relatively strong colorimetric readout, resulting in a relatively significant color change. In comparison, patients with a relatively low level of sulfotransferase activity will have a relatively weak colorimetric readout, and correspondingly a relatively minimal color change. Patients with a strong colorimetric assay response would be expected to respond to minoxidil for hair re-growth or retention. Whereas, patients with a weak colorimetric assay response would be expected to have a poor response to minoxidil.

In another embodiment, the result from a patient's hair follicle colorimetric assay may be used to determine an optimal treatment regime. This may include modifying the concentration and/or frequency of minoxidil therapy to suit the patient's minoxidil sulfotransferase activity. Furthermore, if a patient is unlikely to respond to minoxidil, finasteride may be recommended as an alternative to minoxidil.

With reference to FIG. 1, a method 100 as described herein includes, at 102, collection of a hair follicle sample from a subject. Then, at 104, the hair follicle sample may be coded with a unique identifier, for instance to protect privacy and facilitate handling. At 106, the hair follicle sample may be analyzed as described above. The analysis can be performed using the colorimetric assay described herein. The results of the analysis may then be provided to the subject or to the caregiver of the subject, at 108. The results of the analysis, each associated with its unique identifier, can be transmitted to a computer system that may include a Web-based server that is accessible, with proper authentication for instance using the unique identifier, by the subject or caregiver. The result, in addition to providing an indication of the likelihood that the patient will respond to 2%, 5% or greater minoxidil for the treatment of androgenetic alopecia, may also include a prediction of the dosage required and daily frequency of treatment by comparing a patient's minoxidil sulfotransferase activity level to a reference database.

Figure 2:
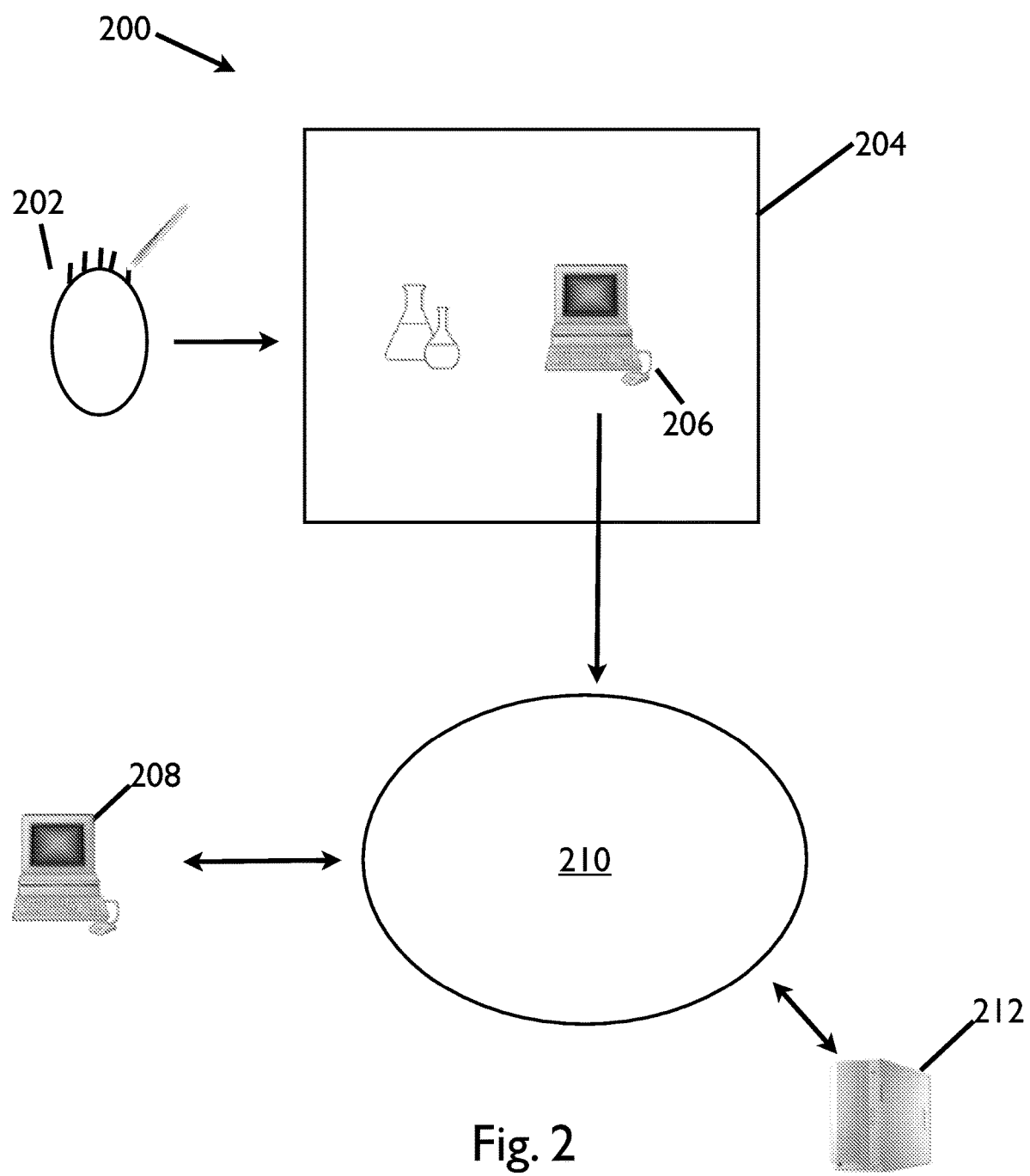
FIG. 2 shows an example of a computerized system for conducting or analyzing an assay to test hair follicles and providing a result.

FIG. 2 schematically shows a system 200 for implementing the above procedure. A sample 202 of hair follicle from a subject is sent to a lab 204. An analysis of the sample in accordance with one or more of the afore-mentioned procedures is then conducted. Results of the analysis are for example compared with a database to generate an indication of the likelihood that the patient will respond to minoxidil for the treatment of androgenetic alopecia. The database may be dynamic in nature, continuously updated for statistical adaptation based on past minoxidil treatment and response thereto, so that the database can adapt, or learn, from the patient pool and treatments over time, and in this manner become a better predictor of the likelihood of responders to the drug treatment. The database, or other entity or circuit or module capable of the adaptive scheme herein described, may reside in computer system 206 or separately therefrom. The outcome of the comparison and analysis can be forwarded to the subject's or caregiver's computer system 208, for example electronically by way of a network, such as the Internet, 210. Alternatively or in addition, the outcome of the comparison and analysis can be stored on a server 212 for accessing remotely by the subject or caregiver following proper authentication that may require reference to the unique identifier to preserve privacy.

It may also be possible to use a neural network to implement the system and method, to predict the likelihood that the patient will respond to minoxidil for the treatment of androgenetic alopecia based on the patient's minoxidil sulfotransferase activity profile. According to such an approach, for predicting the likelihood of response to the drug treatment can include (a) constructing an N-layer neural network, and (b) training the neural network with a data set of patients' outcomes to treatment with minoxidil for androgenetic alopecia along with the patients' minoxidil sulfotransferase activity profiles, (c) obtaining a hair follicle sample from the subject (d) generating a minoxidil sulfotransferase activity profile from the sample, the profile being a function of values associated with a prescribed set of minoxidil sulfotransferase activity levels; (e) inputting the subjects minoxidil sulfotransferase activity profile into the neural network; (f) obtaining a value or set of values from the neural network indicative of the patient's expected outcome (respondent) to the drug treatment at a single or multiple dosages; and (g) providing the patient the drug treatment at the recommended dosage.

It another embodiment, the result from a patient's hair follicle colorimetric assay may be used in conjunction with a genetic test to determine the cause of low follicular sulfotransferase activity. In this case there can be inherited traits that are responsible (genetic) or environmental causes. In the case of genetic traits, it has been reported that variability in sulfation is related to genetic polymorphism in SULT1A1. See Rossi A M, Maggini V, etal., Phenotype-genotype relationships of SULT1A1 in human liver and variations in the IC50 of the SULT1A1 inhibitor quercetin, *Int J Clin Pharmacol Ther.* 2004; 42(10):561-7. In this report an allele of the SULT1A1 (sult1A1*2) gene was reported to drastically reduce the amount of sulfation of a diagnostic substrate. Genotyping patients that test negative with the colorimetric assay can identify sult1A1*2 or other polymorphisms as the root of SULT1A1 deficiency in the scalp. This would be an important determination because environmental conditions can also cause low levels of sulfotransferase activity. For example, salicylic acid has been reported to lower SULT1A1 sulfation of minoxidil by competitive inhibition. See Pacifici G M Inhibition of human liver and duodenum sulfotransferases by drugs and dietary chemicals: a review of the literature. See *Int J Clin Pharmacol Ther.* 2004; 42(9):488-95. If genotyping of a patient indicated that no genetic defects produced low sulfotransferase activity, this would suggest environmental causation and could potentially be remedied. Alternatively, genotyping of SULT1A1 polymorphisms can be used as a primary indicator of likely minoxidil efficacy.

In addition to or instead of SULT1A1 *2, other alleles such as Arg213His (rs9282861 genotype) may be similarly tested, and the results used in the same way. Additionally, polymorphisms in the 5'-flanking region of the SULT1A1 gene have been reported to be associated altered expression of SULT1A1. See Ning B, Nowell S, et. al. Common genetic polymorphisms in the 5'-flanking region of the SULT1A1 gene: haplotypes and their association with platelet enzymatic activity. *Pharmacogenet Genomics.* 2005; 15(7): 465-73. In the report five common genetic polymorphisms (-624G>C, -396G>A, -358A>C, -341C>G and -294T>C) were identified as diagnostic for different SULT1A1 expression levels in platelets.

Figure 3:
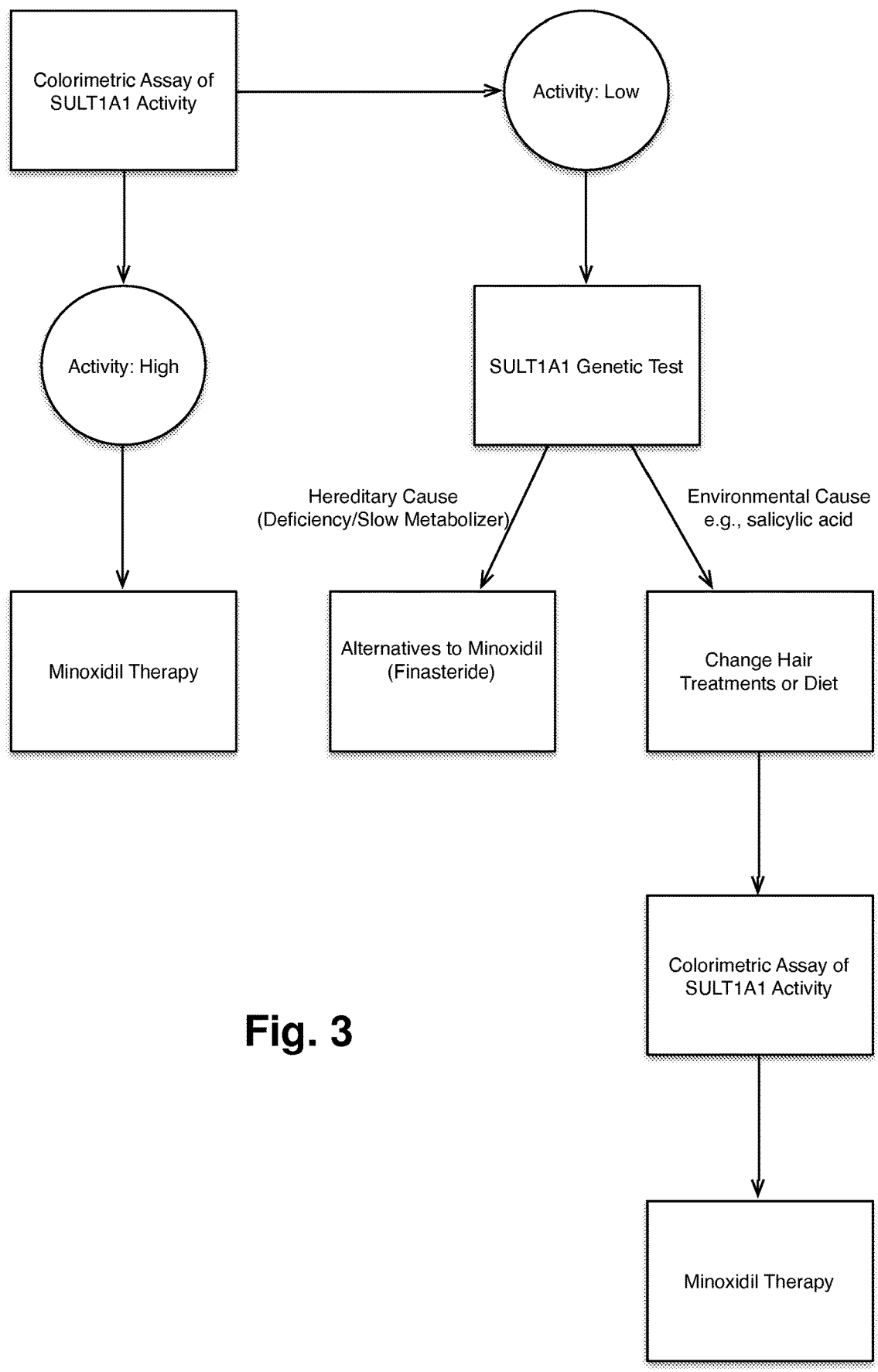
FIG. 3 is a decision flowchart for the indicated use of minoxidil for the treatment of AGA based on a colorimetric assay and genetic tests where indicated.

FIG. 3 schematically shows an example system for implementing the above procedure. In this example, a colorimetric assay of SULT1A1 activity may be performed. If the activity is high, then minoxidil therapy may be prescribed. On the other hand, if the activity is low, a SULT1A1 genetic test may be performed. If it is determined that there is a hereditary cause of the low activity, alternatives to minoxidil (e.g., finasteride) may be prescribed. If there are environmental causes to the low activity, such as salicylic acid, then a change in hair treatments or diet may be prescribed. After some period of time, another colorimetric assay of SULT1A1 activity may be performed, and if activity is high, minoxidil therapy may be prescribed.

Example

SULT1A1 Assay

Minoxidil is converted in the scalp to its active form, minoxidil sulfate, by the sulfotransferase enzyme SULT1A1. SULT1A1 enzyme activity in the hair follicle correlates with minoxidil response for the treatment of AGA. A retrospective study of a SULT1A1 activity assay demonstrates 95% sensitivity and 73% specificity in predicting minoxidil treatment response for AGA.

In this study, patients were selected by a dermatologist (Svenson Medical) from a pool of patients treated with minoxidil mono-therapy for a minimum duration of 6 months. Patient charts were thoroughly documented including global photography at regular intervals. Global photographs were blindly assessed by an independent expert; a standard scale was utilized: (−1) negative response, (0) no response, and (+1) response. Patients with photos (before and after) found difficult to interpret (e.g., changed hair color, style, angle, or lightning) were excluded from the study. In total, 34 patients were included.

Plucked hairs were collected from the border between bald and non-bald scalp and inspected visually for an intact bulb. Hairs were included if they were judged to be in the anagen phase of growth (round bulb). Suitable hairs were trimmed to a length of ~1 cm and immersed, bulb first, in 100 µL of the assay solution (50 mM phosphate buffer (pH 8), 5 mM potassium p-nitrophenyl sulfate, 20 µM adenosine 3',5'-diphosphate, 100 µM minoxidil and 5 mM $MgCl_2$). Hairs were allowed to react with the solution for 24 hours. After incubation, hairs were removed and the optical absorption at 405 nm was determined with a spectrophotometer (Shimadzu UV-1700, Kyoto, Japan) using a single scan and 1 cm path length.

Following the blinded expert assessment of global photographs, data was tabulated (Table 1) based on sulfotransferase activity (i.e., optical density at 405 nm). A cut-off value of less than 0.4 OD was chosen as a marker for low follicular sulfotransferase activity. Based on the 0.4 OD marker, the assay predicts responders to minoxidil therapy with a sensitivity of 95% and a specificity of 73% (Table 2). These results support sulfotransferase activity in the hair follicle as a strong predictor of minoxidil response in AGA patients.

It will be apparent to those of ordinary skill in the art that modifications of the above embodiments can be made without departure from the spirit and scope of the inventions as set forth in the following claims.

TABLE 1

SUMMARY OF MINOXIDIL RESPONSE ASSESSMENT BASED ON SULFOTRANSFERASE ACTIVITY.

| PATIENT | RESPONSE | $OD_{405}$ |
|---|---|---|
| 1 | 1 | 1.348 |
| 2 | 1 | 1.272 |
| 3 | 0 | 1.132 |
| 4 | 1 | 1.100 |
| 5 | 0 | 1.028 |
| 6 | 1 | 1.024 |
| 7 | 1 | 0.956 |
| 8 | 0 | 0.944 |
| 9 | 1 | 0.876 |
| 10 | 0 | 0.832 |
| 11 | 1 | 0.824 |
| 12 | 1 | 0.808 |
| 13 | 1 | 0.752 |
| 14 | 1 | 0.704 |
| 15 | 1 | 0.700 |
| 16 | 1 | 0.684 |
| 17 | 1 | 0.600 |
| 18 | 1 | 0.548 |
| 19 | 1 | 0.484 |
| 20 | 1 | 0.444 |
| 21 | 1 | 0.420 |
| 22 | 1 | 0.416 |
| 23 | 0 | 0.376 |
| 24 | 0 | 0.308 |
| 25 | 0 | 0.288 |
| 26 | 1 | 0.252 |
| 27 | −1 | 0.216 |
| 28 | −1 | 0.200 |
| 29 | 0 | 0.188 |
| 30 | 0 | 0.168 |
| 31 | 0 | 0.148 |
| 32 | 0 | 0.132 |
| 33 | 0 | 0.116 |

TABLE 2

RESPONDER VERSUS NON-RESPONDER SEGREGATION BASED ON SULFOTRANSFERASE ACTIVITY.

|  | OD ≤ 0.4 | OD > 0.4 |
|---|---|---|
| RESPONDER | 1 | 18 |
| NON-RESPONDER | 11 | 4 |

What is claimed is:

1. A method of developing a treatment for a human subject suffering from androgenetic alopecia, comprising:
   obtaining a sample from the human subject, comprising one or more hairs that have been plucked from the human subject, said hairs comprising one or more hair follicles;
   performing a colorimetric assay to measure a sulfotransferase enzyme activity in the sample, thereby generating an activity value indicative of the sulfotransferase activity level in the sample, wherein the assay comprises the step of placing the sample in a reaction mixture comprising an indicator dye and minoxidil, and wherein during the assay, the indicator dye undergoes a color change that correlates with the amount of sulfotransferase activity level in the sample, and wherein the activity value correlates with said color change;
   performing a genetic test on the human subject to determine a cause of the sulfotransferase activity level represented by the activity value, the genetic test comprising genotyping the human subject to identify the presence of a predetermined allele of sulfotransferase;
   comparing the activity value to one or more standardized activity values, each standardized activity value representing either high or low expected minoxidil response for hair re-growth or retention for a class of human subjects including the human subject, thereby producing an indication of either high or low expected minoxidil response for hair re-growth or retention for the human subject at a particular dosage and form of minoxidil; and
   developing an androgenetic alopecia treatment for the human subject based on the high or low expected minoxidil response.

2. The method of claim 1, wherein the indicator dye is p-nitrophenyl sulfate.

3. The method of claim 2, wherein the assay further comprises the steps of:
   placing the sample in a reaction mixture containing about 30 to about 70 mM potassium phosphate buffer with pH between about 6.5 and about 8.0, about 3 to about 7 mM magnesium chloride, about 15 to about 25 µM adenosine 3',5'-diphosphate (PAP) or adenosine 3'-phosphate, 5'-phosphosulfate (PAPS), about 3 to about 7 mM p-nitrophenyl sulfate and about 0.07 to about 0.13 mM minoxidil;
   mixing the reaction mixture which contains the sample, such that a reaction is initiated;
   incubating the sample within the reaction mixture for a predetermined length of time sufficient to bring the reaction to substantial completion; and
   stopping the reaction.

4. The method of claim 3, wherein the assay further comprises adding a basic buffer of about 0.25 M Tris-HCl, pH approximately 8.7 to the reaction mixture to quench the assay.

5. The method of claim 1, wherein generating an activity value is performed by measuring the optical density at approximately 405 nm with a spectrophotometer.

6. The method of claim 5, wherein the one or more standardized values are a cut-off value at which, within a statistical sample of other human subjects, there is a sensitivity of at least about 75% for prediction of positive hair re-growth or retention response to treatment by minoxidil, and a selectivity of at least about 50%.

7. The method of claim 6, wherein the sensitivity is at least about 90%, and the selectivity is at least about 65%.

8. The method of claim 1, wherein the colorimetric assay uses 2-naphthol as a substrate, to improve the sensitivity or specificity of the assay.

9. The method of claim 1, wherein the sample consists of one hair comprising one hair follicle that has been plucked from the human subject.

10. The method of claim 1, wherein the reaction time for the assay is inversely correlated with the number of hair follicles in the reaction.

11. The method of claim 1, wherein the human subject with high sulfotransferase activity is prescribed a low dose of minoxidil and/or a decrease in the frequency of minoxidil application.

12. The method of claim 1, wherein the human subject with low sulfotransferase activity is prescribed a high dose of minoxidil and/or an increase in the frequency of minoxidil application.

13. The method of claim 1, wherein the sulfotransferase is SULT1A1.

14. The method of claim 13, wherein:
   the human subject exhibits low SULT1A1 activity; and
   the genetic testing comprises performing a test of a biological sample from the human subject for the presence of a predetermined polymorphism in the coding or promoter region of the SULT1A1 gene.

15. The method of claim 14, wherein the polymorphism is selected from the group consisting of SULT1A1 *1, SULT1A1 *2, SULT1A1*3, Arg213His, -624G>C, -396G>A, -358A>C, -341C>G, and -294T>C.

16. The method of claim 15, wherein the polymorphism is SULT1A1*2.

17. The method of claim 16, wherein the human subject exhibits the SULT1A1*2 polymorphism, wherein the human subject is prescribed finasteride.

18. The method of claim 16, wherein the human subject does not exhibit the SULT1A1*2 polymorphism, wherein the androgenetic alopecia treatment excludes any use of topical salicylic acid.

* * * * *